United States Patent [19]

Pedersen et al.

[11] Patent Number: 5,532,007
[45] Date of Patent: Jul. 2, 1996

[54] METHOD FOR PRODUCTION OF A MEAT HYDROLYZATE

[75] Inventors: Hanne H. Pedersen, Lyngby; Hans S. Olsen, Holte; Per M. Nielsen, Hillerød, all of Denmark

[73] Assignee: Novo Nordisk A/S, Bagsvaerd, Denmark

[21] Appl. No.: 351,289

[22] PCT Filed: Jun. 30, 1993

[86] PCT No.: PCT/DK93/00215

§ 371 Date: Dec. 8, 1994

§ 102(e) Date: Dec. 8, 1994

[87] PCT Pub. No.: WO94/01003

PCT Pub. Date: Jan. 20, 1994

[30] Foreign Application Priority Data

Jul. 3, 1992 [DK] Denmark .................................. 0876/92

[51] Int. Cl.$^6$ ........................ A23L 1/31; A23J 1/02; A23J 3/00
[52] U.S. Cl. ........................ 426/56; 426/59; 426/656

[58] Field of Search .................. 426/56, 59, 656

[56] References Cited

U.S. PATENT DOCUMENTS

| | | | |
|---|---|---|---|
| 3,970,520 | 7/1976 | Feldman et al. | 426/59 X |
| 4,220,724 | 9/1980 | Berg et al. | 435/273 |
| 5,053,234 | 10/1991 | Anderson et al. | 426/59 |
| 5,077,062 | 12/1991 | Ernster | 426/46 |

FOREIGN PATENT DOCUMENTS

| | | |
|---|---|---|
| WO90/05462 | 5/1990 | WIPO . |
| WO91/18520 | 12/1991 | WIPO . |
| WO93/08702 | 5/1993 | WIPO . |

*Primary Examiner*—Donald E. Ozaja
*Assistant Examiner*—Choon P. Koh
*Attorney, Agent, or Firm*—Steve T. Zelson; Elias J. Lambiris

[57] ABSTRACT

The method comprises a series of steps, with raw meat as a starting material, including a hydrolysis with a specified neutral and alkaline protease. The meat hydrolyzate exhibits excellent organoleptic properties and can be used as a flavoring additive to a soup concentrate.

7 Claims, No Drawings

METHOD FOR PRODUCTION OF A MEAT HYDROLYZATE

CROSS-REFERENCE TO RELATED APPLICATIONS

This application is a continuation of PCT/DK93/00215 filed Jun. 30, 1993, which is incorporated herein by reference.

Hydrolysis of meat in order to manufacture a meat hydrolyzate useable as a food flavoring agent, which can be added to e.g. soup concentrates is an old art. Reference can be made to Japanese patent no. 72-13092 and to "AMPC Product Applications Summary", published by American Meat Protein Corporation, 2325 North Loop Drive, Ames, Iowa 50010, U.S.A.

One of the problems encountered in this area is the organoleptic properties of the meat hydrolyzate, which is open to improvement. Reference can be made to Meat Science 11 (1984) 227–238 (O'Meara & Munro: Effects of reaction variables on the hydrolysis of lean beef tissue by Alcalase®). This reference describes a process for production of a beef meat hydrolyzate, which, however, exhibits an unagreeable degree of bitterness. Documentation will be presented later in this specification. Also, treatment of meat with proteases comprising both endo- and exo-activities belong to the prior art; these meat hydrolyzates also exhibit unsatisfactory organoleptic properties.

Thus, the purpose of the invention is the provision of a method for production of a meat hydrolyzate, which exhibits better organoleptic properties than the hitherto known meat hydrolyzates.

Now, surprisingly it has been found that the purpose of the invention is fulfilled, if raw meat is treated in a specified manner with a special combination of proteases, more precisely stated if raw meat is treated with more than one protease, and if, predominantly, preferably exclusively endo-activities are present during the hydrolysis.

Thus, the method according to the invention for production of a meat hydrolyzate is characterized by the fact that a) raw meat is mechanically pretreated, b) water is added in an amount which makes the mixture of the mechanically pretreated meat and water stirrable and treatable in a centrifuge, c) pH is adjusted to a value between 5.5 and 7.5, d) a neutral protease producible by means of a Bacillus strain and an alkaline protease producible by means of a Bacilllus strain is added in a proportion, which will result in a final meat hydrolyzate with a bitterness below the threshold value for bitterness, and a hydrolysis is carried out to a DH between 3 and 20%, e) the proteases in the hydrolyzed mixture are inactivated by heating, whereby the temperature during the steps a) to d) inclusive does not exceed 70° C., and f) the inactivated mixture from step e) is converted to a fat free meat hydrolyzate.

Surprisingly it has been found that the meat hydrolyzate producible by means of the method according to the invention exhibits extremely good organoleptic properties, which makes the meat hydrolyzate very well suited as flavoring additive to soup concentrates.

In this specification with claims raw meat is defined as meat which is not heat treated to above the denaturation temperature for the proteins of the meat, which is around 70° C., preferably not above 55° C. It is described that raw meat has little odor and only a blood like taste, whereas cooking develops its flavor (vide e.g. J. Agric. Food Chem. 1991, 39, page 344). Thus, contrary to prior art knowledge, the meat to be used in the method according to the invention is raw and not cooked, and even so, excellent organoleptic properties of the resulting meat hydrolyzate is developed. If a heat treatment is carried out before the hydrolysis it has been found that contrary to what should be expected the organoleptic properties of the resulting meat hydrolyzate is unsatisfactory. Also, by meat in this specification, we understand all kinds of animal muscle protein from any animal source. The animal can belong to the cattle or poultry species, and for instance the animals can be cows, pigs, sheep, turkeys, chicken or hens.

The raw meat can originally (i.e. before step a)) be present as meat lumps or bones with meat attached to it. If the raw meat is present as meat lumps the mechanical pretreatment in step a) comprises a mincing to a miximal particle size of around 1 mm; if the raw meat is present as bones with meat attached to it, the mechanical pretreatment in step a) comprises a crushing of the bones to a particle size of around 1 cm to 5 cm.

In step b) water is added in an amount which makes the mixture of the mechanically pretreated meat and water stirrable and treatable in a centrifuge. In more detail, the mixture should be stirrable during the later enzymatic treatment (step d)), and the mixture should be treatable in a centrifuge during the later conversion to a fat free meat hydrolyzate (step f)). If the meat is originally present as meat lumps water should usually be added in an amount of between 25 and 75% of the weight of the meat, and if the meat is originally present as bones with meat attached to it water should usually be added in an amount of between 200 and 1000% of the weight of the meat only, the weight of the crushed (meat free) bones being left out of consideration.

In this specification with claims, especially in relation to step d), a neutral protease is defined as a protease with a pH optimum between 6.5 and 7.5, measured according to the Anson method, and an alkaline protease is defined as a protease with a pH optimum between 8 and 10, measured according to the Anson method. It is to be noted that prior art meat hydrolyzates which are produced by means of at least two enzymes, do always contain both endo- and exo-proteases. In contradistinction thereto, the method according to the invention uses an enzyme system, which comprises endo-proteases only. Also, it has been found that the use of a single enzyme will not give rise to a meat hydrolyzate with satisfactory organoleptic properties.

The inactivation by heating during step e) is carried out at a temperature and during a time interval, which will result in a complete inactivation. Usually temperatures between 90° and 105° C. are used. Also, the temperature during steps a) to d) inclusive is adjusted to values, at which both the activity and the stability are reasonably good. At temperatures above 70° C. the stability tends to be too low. Usually, the temperature during steps a) to d) is between 50° C. and 70° C.

In relation to step f) it can be noted that the conversion to a fat free meat hydrolyzate is performed in a conventional manner.

It is to be understood that the organoleptic properties of the resulting meat hydrolyzate will be impaired, if the time duration of the reaction steps b) to e) is too long. A time duration of maximum around 3 hours yields satisfactory results.

A preferred embodiment of the method according to the invention comprises that in step a) the raw meat is raw beef meat. In this case a meat hydrolyzate with exceptionally good organoleptic properties is obtained.

A preferred embodiment of the method according to the invention comprises that in step b) water is added in an amount of between 40 and 60% of the weight of the raw meat, the meat being present as meat lumps prior to step a). If the amount of added water is less than 40% of the weight of the raw meat, the yield of hydrolyzate tends to be too small, and if the amount of added water is above 60% of the weight of the raw meat, the economy tends to be inferior, due to the costs related to the later removal of the water. Thus, this embodiment exhibits an optimal economy.

A preferred embodiment of the method according to the invention comprises that the pH in step c) is adjusted to between 6.0 and 7.0. If the pH in step c) is below 6.0 the activity of the enzymes tends to be too small, and if the pH in step c) is above 7.0 the organoleptic properties of the resulting hydrolyzate tend to be unsatisfactory.

A preferred embodiment of the method according to the invention comprises that in step d) the neutral protease is producible by means of *B. subtilis*, and the alkaline protease is producible by means of B. licheniformis, B. lentus or B. firmus. These proteases are commercially available and have been found satisfactory.

A preferred embodiment of the method according to the invention comprises that in step f) the conversion to a fat free meat hydrolyzate is performed by centrifugation. In this manner the conversion can be carried out rapidly and effectively.

A preferred embodiment of the method according to the invention comprises that a homogenizing step is performed after step b), but before step f). In this embodiment an increased yield is obtained.

Also, the invention comprises a use of the meat hydrolyzate prepared by means of the method according to the invention, as a flavoring additive to a soup concentrate. The use of an acid catalyzed meat hydrolyzate as a flavoring agent to a soup concentrate and the use of a mixture of an acid catalyzed meat hydrolyzate and an enzyme catalyzed meat hydrolyzate as a flavoring agent to a soup concentrate belong to the prior art, but the use of an enzyme catalyzed meat hydrolyzate without accompanying acid catalyzed meat hydrolyzate is novel. It has been found that the soup concentrate prepared inside the scope of the invention exhibits an excellent flavor.

EXAMPLES 1–13

The following trials, described in Examples 1–13 were carried out in the laboratory to study degree of hydrolysis, protein yield and taste of beef protein hydrolyzates produced with different enzyme combinations. The trials illustrate the necessity of a combination of neutral and alcaline proteases to obtain a non bitter product with beef taste.

Experiments

For all trials the same batch of raw beef meat was used. A big portion of Danish beef trimmings was ground on a meat mincer. The meat was mixed with the half amount of water, and heated to 55° C., and a homogenization was carried out on a Fryma mill. The meat paste was frozen in small portions for the lab trials.

% of protein=12.9 (N×6.25)

DM %=22.4

800 g of meat paste was placed on a water bath in a glass vessel with good agitation. The temperature desired for the trial was obtained, and the pH value was adjusted with NaOH. The enzyme reaction was started by addition of the desired enzyme combination. The actual temperature, pH, reaction time and enzyme combinations used in the individual trials are shown in Table 1. The enzyme preparations used are Neutrase® 0.5 L, Alcalase® 2.4 L and Esperase® 8.0 L. The differences in reaction temperatures used in the trials are due to the optimal conditions for the actual enzyme preparations.

The enzyme reaction was followed by taking out 10 ml samples, centrifuging 1 minute at 4000 rpm, and then measuring osmometer values in the soluble middle phase. The 10 ml sample was returned to the reaction vessel again in order to carry out a final yield calculation. The osmometer values are used to calculate the degree of hydrolysis (DH) during the reaction.

$$DH = \frac{mOSM_{difference}}{S\% * f_{osm}} * \frac{1}{\omega} * \frac{100\%}{h_{tot}}$$

where
$mOSM_{difference}$ is the increase in osmolality measured in milliosmol/kg of water
S % is the protein substrate concentration (N*6.25)
$\omega$ is the osmotic coefficient ($\omega$=0.96 for most actual concentrations of protein)
$f_{osm}$ is the factor which converts % to g per kg of water, determined as $f_{osm}$=1000/(100–D %) where D % is the dry matter %, and
$h_{tot}$ is the number of peptide bonds per weight unit in the protein. For meat $h_{tot}$=7.6 eqv/kg The hydrolysis was stopped by inactivation of the enzymes by heating to 90° C. for 30 min. The heating was performed in a microwave oven, and the vessel was afterwards placed on a boiling water bath.

The total mixture was separated on a centrifuge equipped with 1 l vessels (15 minutes at 4200 rpm).

The total weight of the mixture and the amount of the three phases, i.e. fat, liquid and sludge was determined. DM % and % of protein was measured on the liquid phase.

On the basis of these measurement the yield of protein obtained in the centrifugate in relation to the total amount of protein in the meat can be calculated.

Also the amount of solubilized protein in relation to the total amount of protein in the meat can be calculated (PSI). This quantity expresses the theoretical yield of soluble protein, if the sludge was washed totally free of soluble protein.

$$\text{Protein yield, }\% = \frac{MC * PC\%}{MR * PR\%} \times 100$$

$$PSI, \% = \frac{PC\% * (100 - HR\%)}{PR\% * (100 - HC\%)} \times 100$$

where
MC is the mass of centrifugate
MR is the mass of reaction mixture
PC % is the protein content in the centrifugate
PR % is the protein content in the reaction mixture
HC % is the dry matter content in the centrifugate
HR % is the dry matter content in the reaction mixture Final DH calculated on the basis of osmometer measurements, protein yield and PSI are shown in Table 1.

Taste evaluation

The taste of the beef hydrolyzates was evaluated by a trained taste panel consisting of six persons. The evaluation was carried out in a special taste evaluation room, with separated seats. The soluble protein phase was adjusted to 4.0% protein and tasted at 35° C. The bitterness was tested and evaluated on a scale with the four notes −, +, + +, and + + +. The results are shown in Table 1.

Comments

The use of an alkaline protease alone (Alcalase® or Esperase®) or in combination gives rise to a bitter tasting product (Examples 1–6) even if the final DH is relatively low.

The use of a neutral protease alone (Neutrase®, Example 7) gives rise to a non bitter tasting hydrolyzate, which however exhibits a very flat taste, not at all as meaty as hydrolyzates produced by using neutral and alkaline proteases in combination (Examples 8–13). Also the yield of protein and PSI is much influenced by the above indicated kinds and combinations of enzymes.

The protein hydrolysis was carried out for 1.5 hour, and then the mixture was heated to 90° C. in order to inactivate the enzymes. The high temperature was maintained in the following separation steps.

The protein sludge was removed on a self ejecting centrifuge of the type Westfalia SC-35, and the sludge was collected for washing in a later step.

The centrifugate was passed to a fat separator of the type Westfalia SB-7, where it was defatted. In this step also a small amount of sludge appeared.

Evaporation of the centrifugate was carried out at a Niro falling film evaporator. The concentrate was then spray dried.

Comments

The product obtained has a good taste and the yield is satisfactory.

TABLE 1

| Example no. | T (°C.) | pH | Reaction time (h) | Enzyme dosage % on protein basis | Final DH % | Bitterness | protein yield % | PSI % |
|---|---|---|---|---|---|---|---|---|
| 1 | 65 | 7.0 | 2 | 0.5% Esperase ® | 6.6 | + | 47.4 | 72 |
| 2 | 65 | 7.0 | 2 | 1.0% Esperase ® | 7.6 | ++ | 53.5 | 75 |
| 3 | 65 | 7.0 | 2 | 1.0% Alcalase ® | 11.0 | ++ | 55.7 | 76 |
| 4 | 65 | 7.5 | 4 | 0.5% Esperase ® | 8.8 | ++ | 52.9 | 78 |
| 5 | 65 | 7.5 | 4 | 1.0% Esperase ® | 10.5 | ++ | 59.2 | 83 |
| 6 | 65 | 7.5 | 4 | 0.5% Esperase ® 0.5% Alcalase ® | 12.4 | +++ very bad | 51.7 | 83 |
| 7 | 55 | 7.0 | 2 | 3.0% Neutrase ® | 6.2 | − flat, not as meaty as 8–13 | 40.3 | 63 |
| 8 | 55 | 7.0 | 1.5 | 3.0% Neutrase ® 0.15% Alcalase ® | 7.8 | − | 47.0 | 71 |
| 9 | 55 | 7.0 | 1.5 | 3.0% Neutrase ® 0.15% Esperase ® | 10.2 | − | 42.4 | 70 |
| 10 | 55 | 7.0 | 1.5 | 3.0% Neutrase ® 0.3% Esperase ® | 11.4 | − | 47.6 | 73 |
| 11 | 55 | 7.0 | 1.5 | 3.0% Neutrase ® 0.1% Esperase ® 0.1% Alcalase ® | 10.5 | − | 45.6 | 73 |
| 12 | 55 | 7.0 | 3 | 3.0% Neutrase ® 0.15% Alcalase ® | 9.8 | − | 45.7 | 77 |
| 13 | 55 | 7.0 | 4 | 3.0% Neutrase ® 0.1% Esperase ® 0.1% Alcalase ® | 18.6 | − | 49.7 | 81 |

EXAMPLE 14

The following trial was carried out in pilot plant scale. The process equipment used is relevant for industrial production.

300 kg of raw beef meat was chopped in a meat mincer (3 mm holes). 150 kg of hot water (95° C.) was added and the mixture was heated to 55° C. A homogenization was carried out on a Fryma mill. A smooth paste was obtained.

The mixture was pumped to an agitated tank with heating mantle. The temperature was kept at 55° C. during the enzyme reaction. The pH of the meat slurry was adjusted to 7.0 with NaOH, and was not further adjusted during the process.
Enzymes were added as follows:
3.0% of Neutrase® 0.5 L on protein basis, and
0.15% of Alcalase® 2.4 L on protein basis
Samples were taken out during the reaction for evaluation of osmolality in the soluble phase.

EXAMPLE 15

The following trial was carried out in pilot scale. The raw material was pork bones and beef bones (½:½), collected under hygienic conditions in order to be classified as food grade.

Composition: 37% water, 19% protein (total protein including muscle and collagen), 22% fat, 22% ash 300 kg of bones were crushed in a Wolfking Bone Chrusher to a size of 10–20 mm. 300 kg of water was added and the mixture was heated to 55° C. in a reaction vessel with vigorous agitation. The pH value was 7.2, and the pH value was not adjusted during the following enzyme treatment.
Enzymes were added as follows:
6.0 kg Neutrase® 0.5 L/ton of bones
0.3 kg Alcalase® 2.4 L/ton of bones
Samples were taken out during the reaction for evaluation of osmolality in the soluble phase.

The reaction was carried out for 30 minutes, then the mixture was heated to 90° C. in order to inactivate the enzymes. The high temperature was kept for 20 minutes.

The clean bones were separated on an Algaier Sieve, and the liquid fraction was further separated on a self ejecting centrifuge of the type Westfalia SC- 35 in order to remove insoluble sludge. The centrifugate was passed to a fat separator of the type Westfalia SB-7, where it was defatted.

For the purpose of concentration the centrifugate was evaporated on a Niro falling film evaporator, and finally the protein concentrate was spray dried.

| Example No. and kind of meat | T (°C.) | pH | reaction time (h) | enzyme dosage % on protein basis | final DH % | Bitterness | protein yield % |
|---|---|---|---|---|---|---|---|
| 14 beef meat | 55 | 7.0 | 1.5 | 3.0% Neutrase ® 0.15% Alcalase ® | 12.3 | – | 50–60 |
| 15 beef bones and pork bones | 55 | 7.2 | 0.5 | 3.0% Neutrase ® 0.15% Alcalase ® | 16.8 | – | 26* |
| 16 turkey bones | 55 | 7.0 | 0.5 | 3.3% Neutrase ® 0.17% Alcalase ® | 17.5 | – | 32* |

*on the basis of total protein in the raw material (muscle and collagen protein)

Comments

The product obtained has a non bitter taste.

EXAMPLE 16

The following trial was carried out in pilot scale. The raw material was turkey bones, collected under hygienic conditions in order to be classified as food grade.

Composition: 56% water, 18% protein (total protein including muscle and collagen), 17% fat, 9% ash 300 kg of bones were crushed on a Wolfking Bone Chrusher to a size of 10–20 mm. 300 kg of water was added and the mixture was heated to 55° C. in a reaction vessel with vigorous agitation. The pH value was 7.0, the pH value and was not adjusted during the following enzyme treatment.

Enzymes were added as follows:
6 kg Neutrase® 0.5 L/ton of bones
0.3 kg Alcalase® 2.4 L/ton of bones Samples were taken out during the reaction for evaluation of osmolality in the soluble phase.

The reaction was carried out for 30 minutes, then the mixture was heated to 90° C. in order to inactivate the enzymes. The high temperature was kept for 20 minutes.

The clean bones were separated on an Algaier Sieve, and the liquid fraction was further separated on a self ejecting centrifuge of the type Westfalia SC- 35 in order to remove insoluble sludge. The centrifugate was passed to a fat separator of the type Westfalia SB-7, where it was defatted.

For the purpose of concentration the centrifugate was evaporated on a Niro falling film evaporator, and finally the protein concentrate was spray dried.

Comments

The product obtained has a non bitter taste.

We claim:

1. Method for production of a meat hydrolyzate, wherein
   a) raw meat is mechanically pretreated,
   b) water is added in an amount which makes the mixture of the mechanically pretreated meat and water stirrable and treatable in a centrifuge,
   c) pH is adjusted to a value between 5.5 and 7.5,
   d) a neutral protease producible by means of a Bacillus strain and an alkaline protease producible by means of a Bacillus strain is added in a proportion, which will result in a final meat hydrolyzate with a bitterness below the threshold value for bitterness, and a hydrolysis is carried out to a DH between 3 and 20%,
   e) the proteases in the hydrolyzed mixture are inactivated by heating, whereby the temperature during the steps a) to d) inclusive does not exceed 70° C., and
   f) the inactivated mixture from step e) is converted to a fat free meat hydrolyzate.

2. Method according to claim 1, wherein in step a) the raw meat is raw beef meat.

3. Method according to claim 1, wherein in step b) water is added in an amount of between 40 and 60% of the weight of the raw meat.

4. Method according to claim 1, wherein the pH in step c) is adjusted to between 6.0 and 7.0.

5. Method according to claim 1, wherein in step d) the neutral protease is producible by means of *B. subtilis,* and wherein the alkaline protease is producible by means of *B. licheniformis, B. lentus* or *B. firmus.*

6. Method according to claim 1, wherein in step f) the conversion to a fat free meat hydrolyzate is performed by centrifugation.

7. Method according to claim 1, wherein a homogenizing step is performed after step b), but before step f).

* * * * *